(12) United States Patent
Gizurarson et al.

(10) Patent No.: US 9,168,284 B2
(45) Date of Patent: Oct. 27, 2015

(54) BIOLOGICAL ACTIVITY OF PLACENTAL PROTEIN 13

(76) Inventors: Sveinbjorn Gizurarson, Reykjavik (IS); Hamutal Meiri, Tel Aviv (IL)

( * ) Notice: Subject to any disclaimer, the term of this patent is extended or adjusted under 35 U.S.C. 154(b) by 0 days.

(21) Appl. No.: 13/994,642

(22) PCT Filed: Dec. 14, 2011

(86) PCT No.: PCT/IS2011/050014
§ 371 (c)(1),
(2), (4) Date: Jun. 14, 2013

(87) PCT Pub. No.: WO2012/081040
PCT Pub. Date: Jun. 21, 2012

(65) Prior Publication Data
US 2014/0031274 A1    Jan. 30, 2014

(30) Foreign Application Priority Data
Dec. 14, 2010    (IS) .............................................. 8940

(51) Int. Cl.
*A61K 38/17*    (2006.01)
*C07K 14/47*    (2006.01)

(52) U.S. Cl.
CPC ......... *A61K 38/1709* (2013.01); *C07K 14/4715* (2013.01)

(58) Field of Classification Search
CPC ........... A61K 38/1709; C07K 14/4715; C07K 14/435; C07K 14/4726
See application file for complete search history.

(56) References Cited

U.S. PATENT DOCUMENTS

| | | |
|---|---|---|
| 5,198,366 A | 3/1993 | Silberman |
| 2005/0255114 A1 | 11/2005 | Labat et al. |

FOREIGN PATENT DOCUMENTS

| | | |
|---|---|---|
| WO | 01/55202 A1 | 8/2001 |
| WO | 2007/088543 A1 | 8/2007 |

OTHER PUBLICATIONS

Womenshealth.gov (http://www.womenshealth.gov/pregnancy/you-are-pregnant/pregnancy-complications.htm , Sep. 27, 2010).*
MedicinPlus http://www.nlm.nih.gov/medlineplus/ency/article/001496.htm, accessed Jul. 23, 2014.*
MerckManual-Gestational Diabetes, Oct. 2013.*
WebMD (http://www.webmd.com/diabetes/guide/gestational-diabetes-prevention , copyright 2005-2014).*
WebMD (http://www.webmd.com/baby/preeclampsia-risk , copyright 2005-2014).*
Burger et al., "Placental Protein 13 (PP-13): Effects on Cultured Trophoblasts, and Its Detection in Human Body Fluids in Normal and Pathological Pregnancies," *Placenta* 25:608-622, 2004.
Gilstrap et al., "Clinical Management Guidelines for Obstetrician—Gynecologists: Diagnosis and Management of Preeclampsia and Eclampsia," *ACOG Practice and Bulletin* 33:1-9, Jan. 2002.
Huppertz et al., "Longitudinal Determination of Serum Placental Protein 13 during Development of Preeclampsia," *Fetal Diagnosis and Therapy* 24:230-236, Aug. 28, 2008.
Madazli et al., "Correlation between placental bed biopsy findings, vascular cell adhesion molecule and fibronectin levels in pre-eclampsia," *British Journal of Obstetrics and Gynaecology* 107:514-518, Apr. 2000.
Than et al., "A primate subfamily of galectins expressed at the maternal-fetal interface that promote immune cell death, " *PNAS* 106(24):9731-9736, Jun. 16, 2009.
Than et al., "Isolation and Sequence Analysis of a cDNA Encoding Human Placental Tissue Protein 13(PP13), a New Lysophospholipase, Homologue of Human Eosinophil Charcot-Leyden Crystal Protein," *Placenta* 20:703-710, 1999.
Walker, "Pre-eclampsia," *The Lancet* 356:1260-1265, 2000.
Zhou et al., "Human Cytotrophoblasts Adopt a Vascular Phenotype as They Differentiate: A Strategy for Successful Endovascular Invasion?," *J. Clin. Invest.* 99(9):2139-2151, May 1997.

* cited by examiner

*Primary Examiner* — Louise W Humphrey
*Assistant Examiner* — Tara Martinez
(74) *Attorney, Agent, or Firm* — Seed IP Law Group PLLC

(57) ABSTRACT

The present invention relates to the biological and pharmacological effects of placental protein 13 (PP-13), an effect that may be used as a treatment and/or prevention of preeclampsia and placental insufficiencies, in pregnant female mammals, especially pregnant women. The invention relates to a method to treat female mammals with the purpose to precondition the uterine arteries and prevent and/or reverse the pathological conditions associated with placental insufficiency such as preeclampsia, HELLP and/or eclampsia.

10 Claims, 1 Drawing Sheet

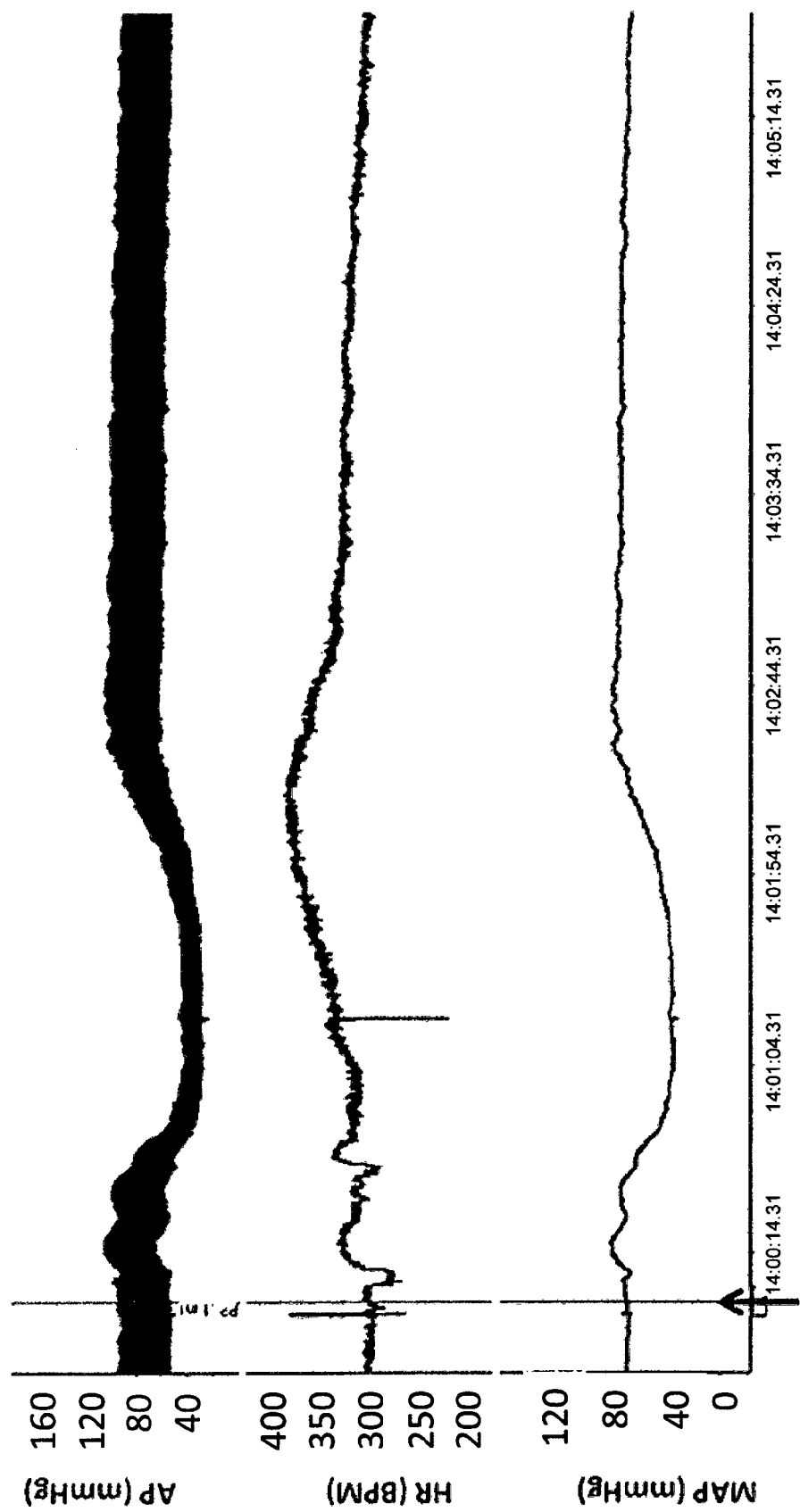

SEQUENCE LISTING

<160> NUMBER OF SEQ ID NOS: 2

<210> SEQ ID NO 1
<211> LENGTH: 139
<212> TYPE: PRT
<213> ORGANISM: Homo sapiens

<400> SEQUENCE: 1

```
Met Ser Ser Leu Pro Val Pro Tyr Lys Leu Pro Val Ser Leu Ser Val
1               5                   10                  15

Gly Ser Cys Val Ile Ile Lys Gly Thr Pro Ile His Ser Phe Ile Asn
                20                  25                  30

Asp Pro Gln Leu Gln Val Asp Phe Tyr Thr Asp Met Asp Glu Asp Ser
            35                  40                  45

Asp Ile Ala Phe Arg Phe Arg Val His Phe Gly Asn His Val Val Met
        50                  55                  60

Asn Arg Arg Glu Phe Gly Ile Trp Met Leu Glu Glu Thr Thr Asp Tyr
65                  70                  75                  80
```

```
Val Pro Phe Glu Asp Gly Lys Gln Phe Glu Leu Cys Ile Tyr Val His
            85                  90                  95

Tyr Asn Glu Tyr Glu Ile Lys Val Asn Gly Ile Arg Ile Tyr Gly Phe
            100                 105                 110

Val His Arg Ile Pro Pro Ser Phe Val Lys Met Val Gln Val Ser Arg
            115                 120                 125

Asp Ile Ser Leu Thr Ser Val Cys Val Cys Asn
        130                 135

<210> SEQ ID NO 2
<211> LENGTH: 578
<212> TYPE: DNA
<213> ORGANISM: Homo sapiens

<400> SEQUENCE: 2
caacacgagg aacaatgtct tctttacccg tgccatacaa actgcctgtg tctttgtctg      60
ttggttcctg cgtgataatc aaagggacac caatccactc ttttatcaat gacccacagc     120
tgcaggtgga tttctacact gacatggatg aggattcaga tattgccttc cgtttccgag     180
tgcactttgg caatcatgtg gtcatgaaca ggcgtgagtt tgggatatgg atgttggagg     240
agacaacaga ctacgtgccc tttgaggatg gcaaacaatt tgagctgtgc atctacgtac     300
attacaatga gtatgagata aaggtcaatg gcatacgcat ttacggcttt gtccatcgaa     360
tcccgccatc atttgtgaag atggtgcaag tgtcgagaga tatctccctg acctcagtgt     420
gtgtctgcaa ttgagggaga tgatcacact cctcattgtt gaggaatccc tctttctacc     480
tgaccatggg attcccagaa cctgctaaca gaataatccc tgctcacatt ttcccctaca     540
ctttgtcatt aaaacagcac caaaactcaa aaaaaaaa                              578
```

BIOLOGICAL ACTIVITY OF PLACENTAL PROTEIN 13

STATEMENT REGARDING SEQUENCE LISTING

The Sequence Listing associated with this application is provided in twxt format in Lieu of a paper copy, and is hereby incorporated by reference into the specification. The name of The text file containing the Sequence Listing is 430192_401USPC_SEQUENCE_LISTING.txt. The text file is 2.3 KB, was created on Sep. 26, 2013, and is being Submitted electronically via EFS-Web.

FIELD OF INVENTION

The present invention relates to the biological, physiological, immunological and pharmacological effect of placental protein 13 (PP-13), its fractions, derivatives and gene expressions. In particular, the invention relates to methods for preventing and/or treating preeclampsia of pregnant female mammal, especially pregnant women. This facilitates and makes possible early clinical intervention when a preeclamptic condition or the risk to develop it is determined with the purpose to cure, reverse or reduce the severity of the pathological disease conditions associated with the disorder.

BACKGROUND OF THE INVENTION

Preeclampsia is a syndrome defined by hypertension and proteinuria developed after twenty (20) weeks of gestation that also may be associated with myriad other signs and symptoms, such as oedema, visual disturbances, elevated liver enzyme, hemolysis, low platelets, headaches, and epigastric pain [1]. One sub-form of the disease, denoted HELLP, standing for hemolysis, elevated enzyme liver and low platelets, can occur with or without hypertension, and the term preeclampsia include this sub-form throughout this document. This disease complicates 3-7% of all pregnancies and is a multisystem maternal disorder that is the most common cause of death for both children and mothers during pregnancy. While the clinical manifestations appear from week 20, the underlying mechanisms may begin as early as at the time of implantation. As the disease progresses the disease may develop into its severe type called eclampsia, caused by angiospasmus in the brain and brain oedema that may result in severe epileptic seizures, stroke and death.

The etiology for preeclampsia is unknown but it is believed that during placentation, the invasion by the placental cells, the trophoblasts, into the uterus wall layer of the spiral arteries appears to be incomplete [2-3] and the severity of hypertension may be related to the degree of trophoblastic invasion [4]. Vasoconstriction and elevated resistance to blood flow follows as a consequence. The etiology is also described as decreased placental perfusion (or placental insufficiency), in combination with oxidative stress that causes general endothelial cell damage within the placenta which may result in endothelial inflammation, affecting the maternal vascular system and the vascularization of the kidneys.

About one third of cases develop in the first pregnancies. Other risk factors include multifetal gestations, conceiving through in-vitro fertilization, particularly oocyte donation, preeclampsia and hypertension disorders in a previous pregnancy, family history of preeclampsia, chronic hypertension, pregestational diabetes, vascular and connective tissue disease, nephropathy, antiphospholipid antibody syndrome, systemic lupus erythematosus (SLE), obesity, age 35 years and older, teenagers and African-American race [5]. Preeclampsia is a leading cause of maternal mortality and morbidity accounting for about 12-18% of all pregnancy-related maternal deaths. It is also associated with a high perinatal mortality and morbidity. The only curative treatment for preeclampsia today is to deliver the fetus and removal of the placenta.

Mothers who develop preeclampsia at pregnancy are at increased risk for cardiovascular diseases and diabetes, and their offsprings are at risk for obesity and diabetes, in addition to developmental disorders such as motor and cognitive disorders and blindness.

Reduced uterine perfusion associated with increased vascular resistance can be detected with Doppler ultrasound of the maternal uterine arteries. The increased impedance to the uterine artery perfusion, or increased pulsatility index and Doppler notch indicates that the mother may have a higher risk of developing preeclampsia, resulting in various endothelial problems such as a general endothelial inflammation. The symptoms of preeclampsia typically appear in the third trimester of pregnancy and are usually detected by routine monitoring of the woman's blood pressure and urine proteins Currently, there are no known cures for preeclampsia except for delivery of the fetus. However, the decision to deliver a patient with preeclampsia must balance both maternal and fetal risks. Preeclampsia can vary in severity from mild to life threatening. A mild form of preeclampsia can remain mild with bed rest and frequent monitoring. For moderate to severe cases, hospitalization is necessary and blood pressure medication and anticonvulsant medications to prevent seizures are prescribed. If the condition becomes life-threatening to the mother or the baby, the only cure is to terminate the pregnancy often resulting in a prematurity of the newborn due to the pre-term delivery. There are two main goals of management of women with preeclampsia: prevention of seizures or eclampsia and control of hypertension. Magnesium sulfate has been used for the prevention of seizures, usually as an intravenous delivery. Daily calcium supplementation and early use of Aspirin may reduce the frequency of the disorder particularly if administered before 16 weeks. Antioxidant vitamins have not been shown to prevent preeclampsia. The management of blood pressure levels with the drugs labetalol or hydralazine has shown benefits although to a limited time.

Novel biomarkers have been found that may be used to detect the syndrome. One such is expressed in the placenta already during the first trimester and may be used to predict pregnancies at risk, a protein called placental protein 13 (PP-13) [6]. The concentration of PP-13 has been shown to be altered in maternal blood in pregnancy disorders such as preeclampsia. More recent studies have shown that the serum levels of PP-13 are significantly reduced at 6-13 weeks in cases developing early, as well as late-onset preeclampsia [7]. PP13 is a member of the β-galactoside binding S-type galectin superfamily and is only expressed in placental tissues of higher primates, and within the villous trophoblast it can only be found in the multinucleated syncytiotrophoblast [8]. PP-13 is expressed and released into the intervillous space, where it enters the maternal circulation and can be detected in maternal blood. While in unaffected pregnancies serum concentrations of PP-13 rise moderately from the first to the third trimester of pregnancy, women who develop preeclampsia start with a lower than normal PP-13 level in the first trimester, and a diagnostic test was develop to use the lower PP-13 level as a measure to predict high risk for preeclampsia. PP-13 levels sharply increase between the first to the third trimester in women who enter the active phase of the disease. This stip change in the level of PP-13 is further assisting in predicting the risk to develop the disorder

SUMMARY OF THE INVENTION

As shown above, there is a need to identify the pregnant subjects at risk of developing pregnancy associated diseases, preferably those at risk of developing preeclampsia and eclampsia, and provide them with the appropriate management regimens. The present invention provides such prevention and/or treatment which has been shown to provide necessary biological effect that will influence the pathophysiology of the disease such as preventing the development of preeclampsia or reducing its severity, when administered into the maternal circulatory system in pregnant women who have been identified to be at risk of suffering from preeclampsia or delivered to the pregnancy in a different way. The best outcome will occur if the pregnant women will receive the treatment, according to the invention, before week 20.

The present invention is based on the inventors' studies on placental protein 13 (PP-13). PP-13 belongs to a group of sugar binding proteins called galectins and they have not been shown to be associated with having cardiovascular, renal or any other biological effect on the stress level. However, this protein or galectin offers more hope of meaningful treatment than any other treatment suggestions available today. Numerous studies on PP-13 have never suggested or associated this protein with recovering the pathophysiology of preeclampsia. Also, the method for diagnosis of pregnant women at risk of developing preeclampsia according to the present invention is very important for this invention. Furthermore, the method for monitoring the progression or regression of the risk factor before week 20 is also important for this invention, in order to help pregnant women to avoid preeclampsia or eclampsia with all the serious risks involved both for the women and/or the fetus.

Surprisingly, PP-13 has been found to cause dilation of arteries and veins, resulting in reduced vascular resistance and preconditioning of the arteries as well as local angiogenesis in uterine arteries and decrease the stress level following administration to a female mammal. Unexpectedly, this is exactly what is needed or what is missing in those women diagnosed with preeclampsia not the active stage of the disease but also in its pre-clinical stage when the underlying pathology is developed. Interestingly, this vasodilation occurs already in the first trimester, forming the connection between low PP-13 and high Doppler impedance as were identified in women at risk to develop preeclampsia. There is a need for a drug or a treatment that may be used as soon as early signs of elevated risk of developing preeclampsia are identified, preferentially as soon as pregnancy is detected, after conception. The optimal start of treatment should occur as soon as low levels of PP-13 has been detected e.g. in week 5-20, preferably in week 6-18 or more preferably in week 7-16.

DETAILED DESCRIPTION

In a first aspect, the invention provides a compound for use as a medicament to affect the pathophysiology of pregnancy to prevent pregnancy associated disease in humans (women) such as but not limited to preeclampsia and/or eclampsia, characterized in that the compound is related to placental protein 13 (PP-13). The compound is preferably human PP-13, most preferably the native full-length protein (as expressed in human tissue) but can also be an active subunit, fragment or derivative thereof.

In another aspect, the invention provides a method of preventing or treating pregnancy associated disease in a female person comprising administering to said person a compound related to PP-13. The pathophysiology affected by the invention can in some embodiments be the physiology of the disease related but not limited to any of the cardiovascular system, renal system, immune system and/or psychology of the disease. Preferably, the compound affects physiology associated with uterine vascularization.

PP-13 to be used according to the invention can be derived from a suitable source, such as human placenta tissue, or over expressed in human or animal cell culture or transgenic organisms or cells expressing human PP-13.

Burger et al. [9], the teachings of which are hereby incorporated in full, disclose the full sequence of human PP-13 protein and its encoding nucleotide sequence, and teach how the protein can be overexpressed in bacterial cell culture, and isolated and purified. In useful embodiments of the invention other cell cultures are used for the overexpression of PP-13, such as but not limited to cells of human origin, animal cells, fungal cells, or plant cells, or in transgenic organisms such as transgenic animals including mice, pigs, cows, or transgenic plants. In one embodiment the protein is expressed and isolated from BeWo cells, which are regularly used as a cell culture model to mimic in vivo syncytialisation of placental villous trophoblast.

The protein comprises 139 amino acids and has a molecular weight of about 16 kDa (calculated 15.6 kDa). The protein sequence is depicted in the enclosed sequence listing as SEQ ID NO:1 and its encoding cDNA sequence as SEQ ID NO:2 (starting codon at position 15). The PP-13 protein is found in the body as a 32 kDa dimer protein, secreted to the extracellular fluid of the placenta and reaching the maternal blood circulation the amniotic fluid and urine. Both the monomer and dimer as well as oligomers can be used in accordance with the present invention. The protein is expressed in and may be isolated from the placenta and its various layers, from syncytiotrophoblasts, extravillous trophoblasts and chorionic villus from the placenta.

The protein as found in the human body is glycosylated and in preferred embodiments, glycosylated forms are used in the present invention, i.e. glycosylated monomer, dimer or fragment; however non-glycosylated forms are also useful and within the scope of this invention, such as those forms that are expressed in expression systems not capable of protein glycolysation. In some of the accompanying examples, non-glycosylated PP-13 is used, expressed in bacterial expression systems, and these forms exhibit activity in accordance with the invention.

In useful embodiments of the invention, derivatives of PP-13 are used, such as but not limited to PEGylated derivatives that may include PEGylated native protein, or PEGylated subunits or fragments. PEGylation refers to the covalent attachment of polyethylene glycol polymer chains to the protein. Methods for PEGylating proteins are well known to the skilled person, see e.g. Fee [10].

The compound and methods of the present invention provide for various routes of administration in accordance with the present invention. These include but are not limited to injections (intravenous, intradermal, subcutaneous, or uterine injections), infusions, nasal, pulmonal, rectal, vaginal delivery or administered via cervix or any transdermal or under-dermal device.

Administration of PP-13 will, according to the invention, provide a preconditioning of arteries and angiogenesis as well as an endothelial effect and/or neuronal effect on the uterine vascularization, arteries and/or veins, causing them to dilate and provide and prepare the uterus for the need of receiving increased flow of blood to support, among others, the rapid fetal growth after week 20 in pregnancy.

Administration of PP-13 will, according to the invention, provide a preconditioning of arteries and angiogenesis, an endothelial effect and/or neuronal effect on the systemic vascularization, arteries and/or veins, causing them to dilate, resulting in lower vascular resistance and lower the systemic blood pressure, both systolic as well as diastolic blood pressure, to provide the optimal blood pressure for the placenta, kidneys as well as other organs to function properly during pregnancy. The vasodilation in the kidney and other nonreproductive organs is one of the earliest maternal adaptation's to occur during pregnancy. The administration of PP-13, according to the invention, provides an endothelial effect and/or neuronal effect on the kidney vascularization, arteries and/or veins, causing them to dilate, which is very important to occur before the end of the first trimester. The low level or lack of PP-13, according to the invention, cannot provide the necessary changes in glomerular filtration rate or in the tubular re-absorption before the week 20 after conception unless the maternal body is provided with external administration of PP-13 to prepare the kidneys for the necessary changes.

According to the invention, administration of PP-13 affects the stress level of the mother, by causing central nervous system (CNS) effect and/or affecting the adrenal gland that produces glucocorticoids making the pregnant women more relaxed and prepared for the remaining pregnancy time.

Administration of PP-13 should occur as often as necessary, such as once or more often, and up to unlimited times. Preferably regularly, in a regimen range from a daily dose to a weekly basis, to provide the maternal body with the necessary amount of the protein. The dose should preferably be calculated according, but not limited to following formula:

$$D = (C_{desired} - C_{actual}) \cdot V_d \cdot W$$

where D is the dose; $C_{desired}$ is the desired PP13 plasma concentration; $C_{actual}$ is the actual PP-13 plasma concentration; $V_d$ is the volume of distribution and W is the body weight. Calculations may need to be adjusted based on serum creatinin, renal clearance, albumin and/or other biological parameters.

In a preferred embodiment, the mammal is a human (women).

In certain embodiments, the compound of the invention is administered in doses that provide a serum concentration of PP-13 in the range of 100-600 pg/mL, preferably in the range of about 150-300 pg/mL and more preferably a concentration in the range of about 175-260 pg/mL. Preferably the compound is administered in a dose that provides equivalent serum concentrations of PP-13 in the range of about 100-600 pg/mL, preferably in the range of about 150-300 pg/mL placental protein 13. Administration of PP-13according to the invention may be carried out alone or in combination with other biologically active compounds such as, but not limited to, relaxin, 17β-estradiol, and/or progesterone.

Such concentrations can be suitably obtained with dose concentrations in injection solutions in the range of about 1-10 μg/mL, such as in the range 2-6 μg/mL, such as about 2, 3, or 5 μg/mL. Suitable injection doses of such injection formulations would be in the range of 200 μL-2 mL, such as in the range 0.5-1 mL.

In embodiments using nasal spray devices, doses in the range of 50-200 μL, such as about 100 μL can be suitable delivered in one or two puffs, as illustrated in the accompanying examples.

In embodiments using vaginal pasery, doses in the range of 5-200 μL, such as about 50 μL can be mixed with a vaginal gel to be suitable for being delivered in one, two or daily use, similar to the way progesterone is used to prevent preterm delivery.

Furthermore, administration of PP-13 may be used in accordance with this invention to preconditioning of arteries in general, especially arteries such as in the heart in both males and female as well as to use PP13 or its derivatives to induce angiogenesis in specific regions of the body such as the brain or the heart in both males and females.

EXAMPLES

PP-13 used in each experiments was a purified human PP-13, expressed in cell culture and/or bacterial culture (*E. coli*), produced (isolated and purified) by Hy-Labs, Ltd. Rehovot, Israel (www.hylabs.co.il).

Example 1

A group of rabbits received 15 ng/kg PP-13 diluted in saline. The administration occurred into the marginal ear vein, slowly over 30 seconds. The animals were observed and sampled for blood samples over the following hours.

Results: The volume of distribution was found to be 221,9 mL/kg and the half-life was found to be 10,6 hours. Within 5 minutes from the beginning of the intravenous drug administration the behavior of the animals changed from being very alert to being relaxed, calm and did not run away when approached for the next blood sample.

Discussion: PP-13 affects the stress levels and makes the animals relaxed and peaceful, which is an important function of PP-13 during pregnancy.

Example 2

Formulations of PP-13 are produced using purified PP-13 (3,0 ug/mL) and PEGylatedPP-13 (equivalent to 3,0 μg/mL of pure PP-13) in saline. About 1 mL of these solutions was administered slowly intravenously to pregnant women in week 11, having the PP-13 levels around 20 pg/mL. Subsequent blood sampling showed that the final serum concentration, 1 hour after the administration is about 200 pg/mL. The women having purified PP-13 require additional doses daily until week 20 from conception, whereas the women receiving PEGylatedPP-13 required additional doses on weekly intervals.

Example 3

A formulation of PP-13 is produced using purified PP-13 (60 μg/mL) and PEGylatedPP-13 (equivalent to 60 μg/mL of pure PP-13) in saline containing 2% methoxypolyethyleneglycole (mPEG 350). The formulation is placed into a multidose nasal spray bottle. Twice daily, the pregnant women who has low serum PP-13 or carry at least one major risk factors to preeclampsia (or two mild ones, stratified according to the WHO) use one puff (about 0,1 mL or 6 μg) of these solutions in week 11, having the PP-13 levels around 20 pg/mL. Subsequent blood sampling showed that the final serum concentration, 1 hour after the administration is about 200 pg/mL. The women having PEGylatedPP-13 needed only one puff per day until week 20 from conception, pregnancy age predefined by last menstrual period or ultrasound dating of pregnancy.

Example 4

Samples are collected from pregnant women. The pregnant woman may be an individual who has been determined to have a high risk of preeclampsia based on her personal or family history or other risk factors as defined by the WHO and/or after determination of the woman's low level PP-13.

A formulation of PP-13 is produced and administered to cervix using pharmaceutically acceptable techniques and formulations in such a way that PP-13 is absorbed through cervix into the uterus.

Example 5

A 244 g rat was anaesthetized with Brietal (50 mg/kg) followed by Inactin (110 mg/kg). After anesthesia the rat was prepared and equipped with blood pressure meter (intra-arterial) on a temperature controlled plate to keep her temperature around 37° C. When the blood pressure was stable (about 45-60 min) the rat received IV dose of 0.1 ml of PP-13 solution (Dose=15 ng). The results obtained are shown in FIG. 1, illustrating a blood pressure lowering effects of PP-13according to the invention, where the top line shows the blood pressure, the middle line show the pulse and the lowest (dotted) line shows the mean arterial pressure.

Example 6

PP-13 was placed into an Alzet osmotic pump system releasing about 0.14 ng/min. The pumps were placed surgically into gravid female 15 week old Sprague-Dawley rats where the controls received the pumps with saline. Blood PP-13 periodically determined on blood samples and urine collection.

The PP-13 group had significantly lower systolic and diastolic blood pressure than the control animals. At the same time the heart rate increased significantly in the PP-13 group indicating that a general vasodilatation had occurred, reducing the peripheral resistance by about 35%. The placenta also showed angiogenesis.

References

1. ACOG Practical Bulletin. Clinical Management Guidelines for Obstetrician-Gynecologists: Diagnosis and management of preeclampsia and eclampsia, Number 33, January 2002 p. 159-167.
2. Zhou Y, Fisher SJ, Janatpour M, Genbacev O, Dejana E, Wheelock M et al. Human cytotrophoblasts adopt a vascular phenotype as they differentiate: a strategy for successful endovascular invasion? J Clin Invest 1997; 99: 2139-2151.
3. Fox H. The placenta in pregancy hypertension. In: Rubin PC ed handgook of hypertension, volume 10: hypertension in pregnancy. New York: Elsevier 1988: 16-37.
4. Madazli R, Budak E, Calay Z, Aksu MF. Correlation between placental bed biopsy findings, vascular cell adhesion molecule and fibronectin levels in pre-eclampsia. BJOG 2000, 107, 514-518.
5. Walker JJ. Pre-eclampsia. Lancet 2000; 356, 1260-1265.
6. Than NG, Sumegi B, Than GN, Berente Z, Bohn H. Isolation and sequence analysis of a cDNA encoding human placental tissue protein 13 (PP13), a new lysophospholipase, homologue of human eosinophil Charcot-Leyden crystal protein. Placenta 1999; 20, 703-710.
7. Huppertz B, Sammar M, Chefetz I, Neumaier-Wagner P, Bartz C, Meiri H. Longitudinal determination of serum placental protein 13 during development of preeclampsia. Fetal Diagn Ther 2008; 24, 230-236.
8. Than NG, Romero R, Goodman M, Weckle A, Xing J, Dong Z et al. A primate subfamily of galectins expresssed at the maternal-fetal interface that promote immune cell death. Proc Natl Acad Sci USA 2009; 106, 9731-9736.
9. Burger O, Pick E, Zwickel J, Klayman, M, Meiri H, Slotky R, Mandle S, Rabinovitch L, Paltieli Y, Admon A, Gonen, R. Placental Proten 13 (PP-13): Effects on Cultured Trophoblasts, and Its Detection in Human Bodu Fluids in normal and Pathological Pregnancies. Placenta 2004, 25, 608-622.
10. Fee, C. J. (2009), "Protein conjugates purification and characterization", PEGylated Protein Drugs: Basic Science and Clinical Applications, Veronese, F. M., Ed. Birkhauser Publishing: Basel, 113-125.

The invention claimed is:

1. A method for treating a pregnancy associated disease selected from eclampsia and preeclampsia in a pregnant female person who is at risk of developing said pregnancy associated disease, comprising administering to said person a composition selected from human placental protein 13 (PP-13) and PEGylated human PP-13, wherein said administering is initiated during weeks 5-20 of pregnancy.

2. The method according to claim 1, wherein the composition is PEGylated human placental protein 13.

3. The method according to claim 1, wherein said composition is administered using an administration route selected from injections, infusions, nasal, pulmonal, rectal, vaginal or administered via cervix or a transdermal or underdermal device.

4. The method according to claim 1, wherein the composition is administered in a dose that provides a serum concentration of PP-13 in a range of about 60-600 pg/mL, for a singleton pregnancy, or an adjusted amount for a twin or multifoetal pregnancy.

5. The method according to claim 1, wherein the composition is administered in a dose that provides equivalent serum concentrations of PP-13 in a range of about 60-600 pg/mL placental protein 13.

6. The method according to claim 1, wherein the composition is administered by a route selected from intravenous, subcutaneous, uterine injection or infusion, nasal delivery, pulmonal delivery, rectal delivery, vaginal delivery and via cervix.

7. The method according to claim 1, wherein the compound is delivered as a controlled release formulation selected from the group consisting of implants, patches, through a pump, microprocessor controlled pump, theranostic delivery system, microparticles, nanoparticles, cell based delivery system that is administered to pharmaceutically acceptable location such as subcutaneous, intramuscular, intraperitoneally, intravaginally and/or into the amniotic fluid where appropriate amount of the compound is released until the pregnancy is over.

8. The method according to claim 4, wherein the compound is administered in a dose that provides a serum concentration of PP-13 in the range of about 90-250 pg/mL, given this is a singleton pregnancy, or the adjusted amount when this is twin or multifoetal pregnancy.

9. The method according to claim 4, wherein the compound is administered in a dose that provides a serum concentration of PP-13 in the range of about 125-200 pg/mL, given this is a singleton pregnancy, or the adjusted amount when this is twin or multifoetal pregnancy.

10. The method according to claim 5, wherein the compound is administered in a dose that provides equivalent serum concentrations of PP-13 in the range of about 100-250 pg/mL placental protein 13.

* * * * *